United States Patent [19]

Jones

[11] 4,377,492
[45] Mar. 22, 1983

[54] POST EMULSIFIABLE FLUORESCENT PENETRANT

[75] Inventor: John P. Jones, Long Beach, Calif.

[73] Assignee: Purex Corporation, Lakewood, Calif.

[21] Appl. No.: 184,945

[22] Filed: Sep. 8, 1980

[51] Int. Cl.³ ...................... C09K 11/00; G01N 21/00
[52] U.S. Cl. ............................................... 252/301.19
[58] Field of Search ....................... 252/301.16, 301.19

[56] References Cited

U.S. PATENT DOCUMENTS

| Re. 28,605 | 11/1975 | Alburger | 106/19 |
|---|---|---|---|
| 2,352,810 | 7/1944 | Swain | 260/22 R |
| 2,794,747 | 6/1957 | Bloch | 106/28 |
| 3,436,959 | 4/1969 | Redemann et al. | 73/104 |
| 3,520,713 | 7/1970 | Sola et al. | 106/27 X |
| 3,546,127 | 12/1970 | Mlot-Fijaikowski | 73/104 X |
| 3,615,750 | 10/1971 | Blair | 106/27 |
| 3,957,495 | 5/1976 | Teranishi et al. | 106/19 |
| 3,981,185 | 9/1976 | Molina | 73/104 |
| 4,108,671 | 8/1978 | Richlin | 106/22 |
| 4,157,947 | 6/1979 | Borden et al. | 204/159.23 |

Primary Examiner—F. Edmundson
Attorney, Agent, or Firm—William W. Haefliger

[57] ABSTRACT

A post emulsifiable penetrant composition for applications and entry into flaws in solid surfaces consists essentially of
 (a) a first solvent ingredient comprising a high boiling point aromatic hydrocarbon,
 (b) a second solvent ingredient selected from the group that includes di-phthalates and diesters,
 (c) epoxidized material selected from the group that consists of epoxidized esters, oils and resins,
 (d) fluorescent dye, and
 (e) fluorescent brightener.

11 Claims, No Drawings

POST EMULSIFIABLE FLUORESCENT PENETRANT

BACKGROUND OF THE INVENTION

This invention relates generally to fluorescent penetrant compositions, and particularly to heat stable compositions of this class.

Many type penetrants have in the past been used to locate flaws or discontinuities in metallic and non-metallic surfaces. The usual method of application is to apply the penetrant to the surface and after a suitable time the excess penetrant is removed by washing with a suitable solvent system or mechanically by wiping with a cloth or other absorbent material. Flaws are subsequently revealed by a seepage of the penetrant from the crevice or cavity. Various agents have been added to the penetrant to increase the visibility of the seepage. These include ordinarily visible dyes, and fluorescent dyes. Absorbent powders are often applied to the surface of the article to absorb some of the dye and thus to increase the visibility of the flaw.

Fluorescent type penetrants which are currently available tend rapidly to lose brightness on metal surfaces when exposed to temperatures greater than about 140° F.; and typically such penetrants lose about 75% or more brightness in about 30 minutes. Accordingly, minute flaws or cracks in the metal surface can and do go undetected, in many cases due to rapid fading. The term "brightness" as used herein refers to visibility under ultraviolet light.

SUMMARY OF THE INVENTION

It is a major object of the invention to provide a solution to the above problem through the provision of an improved penetrant composition, or class of compositions, which retain desired brightness and typically lose less than 50% of their brightness under the same temperature and time conditions wherein prior fluorescent penetrants lose 75% or more of their brightness.

The improved post emulsifiable penetrant composition for entry into flaws or minute cracks is solid metal surfaces consists essentially of:

(a) a first solvent ingredient comprising a high boiling point aromatic hydrocarbon,
(b) a second solvent ingredient selected from the group that includes di-phthalates and diesters,
(c) epoxidized material selected from the group that consists of epoxidized esters, oils and resins,
(d) fluorescent dye, and
(e) fluorescent brightener.

It has been found that the higher boiling point aromatic solvent serves to reduce viscosity of the formulation and provides heat stability. The viscosity reducing property of the aromatic solvent is important due to the viscosity increasing property of the epoxidized vegetable oil ingredient; however the vegetable oil serves to provide desired heat stability.

As respects the aromatic solvent, it consists principally of substituted benzenes and bicyclic aromatics, examples being listed as follows:

| Commercial Identification | Manufacturer |
| --- | --- |
| PANASOL AN-2K | Amoco Chemical Corp. |
| PANASOL AN-3 | Amoco Chemical Corp. |
| Amsco-Solv E 95 | Union Oil Company, California |
| Hi sol 4-1 | Ashland Chemical Company |
| Chartersol 4-P | Charter International Oil Company |
| Aromatic Solvent R | Union Oil Company |

Physical characteristics of the aromatic solvent are: initial boiling point ranging from 350° F. to 450° F. (ASTM D-86); end boiling point ranging from 530° F. to 600° F.; and aromatic content from 75% to 100%. (ASTM D-1319).

As respect the second solvent ingredient, it preferably consists of dioctyl phthalate (also known as di(2-ethylhexyl) phthalate). Other usable phthalates include: diethyl phthalate, dibutyl phthalate, diisodecyl phthalate, diisooctyl phthalate, and di(n-octyl, N-decyl) phthalate. In general, the higher molecular weight phthalates have better heat stability than the lower molecular weight phthalates.

Other diesters, such as adipates, and sebecates (e.g. dioctyl sebecate) may be used, but at some sacrifice of heat stability.

The epoxidized ingredient imparts heat resistance, and consists of an epoxidized ester or oil. A preferred material is epoxidized soybean oil (vegetable oil) such as DRAPEX 6.8, for example, a product of Witco Chemical Co. Other examples are:

| Commercial Identification | Manufacturer |
| --- | --- |
| FLEXOL PLASTICIZER LOE (an epoxidized linseed oil) | Union Carbide Company |
| DRAPEX 3.2 (an octyl stearate epoxy) | Witco Chemical Company |
| DRAPEX 4.4 (an octyl tallate epoxy) | Witco Chemical Company |
| MONOPLEX S-73 (epoxy ester) | Rohm and Haas Company |
| PARAPLEX G-62 | Rohm and Haas Company |

Also, liquid epoxy resins can be used to impart heat stability. An example is BAKELITE ERL 4289, a cycloaliphatic epoxy resin, obtainable from the Union Carbide Company.

A typical formulation is as given in the following table:

TABLE 1

| Ingredient | Range (% by wt) | Preferred (% by wt) |
| --- | --- | --- |
| high boiling point aromatic solvent (example: PANASOL AN-3) | 1–40 | 23.0 |
| di-phthalate solvent or di-ester solvent (example: dioctyl phthalate) | 20–80 | 54.0 |
| epoxidized material (example: DRAPEX 6.8) | 10–25 | 18.0 |
| fluorescent dye (example: a napthalimide such as Hudson yellow) | 0.1–3.0 | 1.0 |
| fluorescent brightener (example: Hiltamine Arctic White Sol, or other coumarin derivative, or MDAC | 0.1–4.5 | 4.0 |

It is found that without expoxidized material in the composition, the fluorescent dye rapidly fades in presence of heat over 130° F. Substitute fluorescent dyes include naphthalimide types such as Fluoral 7GA of GAF Company or Hudson yellow from Day Glo Color Corporation together with a fluorescent brightening agent such as 4-methyl -7-dimethylamine-coumarin (MDAC) or 7-diethylamino-4-methyl coumarin, e.g. Hiltamine artic white SOL of Hilton Davis Corp.

The following formulas are usable, as examples:

FORMULA 1

| Ingredients | % by weight |
|---|---|
| Panasol AN3 | 10.0 |
| di ethyl phthalate | 27.0 |
| di octyl phthalate | 47.0 |
| Drapex 6.8 | 13.5 |
| Hudson yellow | 1.0 |
| Hiltamine arctic white SOL | 1.5 |
| | 100.0 |

FORMULA 2

| Ingredients | % by weight |
|---|---|
| Amaco solv. E95 | 24.0 |
| di octyl sebecate | 55.0 |
| Drapex 6.8 | 18.0 |
| Hudson yellow | 1.0 |
| MDAC | 2.0 |
| | 100.0 |

FORMULA 3

| Ingredients | % by weight |
|---|---|
| Aromatic solvent R | 24.0 |
| di octyl phthalate | 50.0 |
| Drapex 6.8 | 9.0 |
| di ethyl phthalate | 5.0 |
| Monoplex S73 | 9.0 |
| Hudson Yellow | 1.0 |
| Hiltamine arctic white SOL | 2.0 |
| | 100.0 |

FORMULA 4

| Ingredients | % by weight |
|---|---|
| Panasol AN-2K | 24.0 |
| di octyl phthalate | 55.0 |
| Bakelite ERL-4289 | 18.0 |
| Hudson yellow | 1.0 |
| Hiltamine arctic white SOL | 2.0 |
| | 100.0 |

To test for heat stability, nickle chrome test panels with cracks therein (obtainable from Eishin Kagaku Company, Inc.) are processed as follows: penetrant is applied, and after 10 minutes the panels are immersed for 60 seconds in an emulsifier (Group V of Mil-I-25135C). The panels are then rinsed for 120 seconds in water, issuing from a tap at 20 psi. The panels are then force air dried for 5 minutes at 130° F. Developer is applied (for example Fluro-chek DD-2) with 10 minutes dwell. The panels are then examined under ultraviolet light (for comparison purposes, two penetrants may be applied side by side on a panel). The panels are then placed in a forced air stream kept at 150° F., for 30 minutes (for example). They are then again viewed under black light. The two penetrants may then be compared as to fading properties. Typical cracks which can now be visibly seen using the above formulas, but which could not be seen before, have the following characteristics:

width of crack:0.3-2 microns depth of crack:about 50 microns

It should be noted that heating the panels after application of the developer is not a normal process procedure and is for comparison purposes only. Normally, the panel would be heated before the developer is applied. Comparisons can, of course, also be made this way.

I claim:

1. A post emulsifiable penetrant composition for application and entry into flaws in solid surfaces, consisting essentially of
   (a) 1-40 percent, by weight, of a first solvent ingredient comprising an aromatic hydrocarbon having a boiling point within the range of from about 350° F. to about 600° F.,
   (b) 20-80 percent, by weight, of a second solvent ingredient selected from the group that consists of phthalates,
   (c) 10-25 percent, by weight, of epoxidized material selected from the group that consists of epoxidized soybean oils,
   (d) 0.1-3.0 percent, by weight, or fluorescent dye, and
   (e) 0.1-4.5 percent, by weight, of fluorescent brightener,
   (f) said weight percentages adjusted to produce visible fluorescence under blacklight in a groove of the following dimensions,
      (i) width about 0.1-2 microns
      (ii) depth about 10-50 microns.

2. The composition of claim 1 wherein the first solvent is selected from the group that consists of: PANASOL AN-3, PANASOL AN-2K, Amsco-Solv E 95, Hi sol 4-1, Chartersol 4-P, and Aromatic solvent R.

3. The composition of claim 1 wherein the first solvent consists of PANASOL AN-3.

4. The composition of claim 3 wherein said second solvent consists of dioctyl phthalate.

5. The composition of claim 1 wherein said second solvent is selected from the group that consists essentially of dioctyl phthalate, diethyl phthalate, dibutyl phthalate, diisodecyl phthalate, diisooctyl phthalate, di(n-octyl, N-decyl) phthalate.

6. The composition of claim 5 wherein said epoxidized material consists essentially of DRAPEX 6.8.

7. The composition of claim 4 wherein said epoxidized material consists of DRAPEX 6.8.

8. The composition of claim 6 wherein said fluorescent dye consists of a naphthalimide.

9. The composition of claim 8 wherein said naphthalimide consists of Hudson yellow.

10. The composition of claim 1 wherein said fluorescent brightener consists of an MDAC or other coumarin derivative such as Hiltamine Arctic White SOL.

11. The composition of claim 1 wherein the weight percentage of said (a)-(e) ingredients are:
    (a) about 23.0
    (b) about 54.0
    (c) about 18.0
    (d) about 1.0
    (e) about 4.0.

* * * * *